United States Patent

Seino et al.

[11] Patent Number: 5,508,274
[45] Date of Patent: Apr. 16, 1996

[54] 24R,25-DIHYDROXYCHOLECALCIFEROL TO TREAT VITAMIN D RESISTANT RICKETS

[75] Inventors: Yoshiki Seino, Osaka; Hiroyuki Tanaka, Okayama; Yumiko Nagai, Tokyo, all of Japan

[73] Assignees: Kureha Chemical Industry Company, Ltd., Tokyo; Yoshiki Seino, Osaka, both of Japan

[21] Appl. No.: 338,790

[22] Filed: Nov. 8, 1994

Related U.S. Application Data

[63] Continuation of Ser. No. 79,551, Jun. 22, 1993.

[30] Foreign Application Priority Data

Jun. 23, 1992 [JP] Japan ................................. 4-188672

[51] Int. Cl.$^6$ ................................................. A61K 31/59
[52] U.S. Cl. .......................... 514/167; 552/653; 514/170; 514/171; 514/168
[58] Field of Search ........................... 552/653; 514/167, 514/168, 170, 171

[56] References Cited

U.S. PATENT DOCUMENTS

| | | | |
|---|---|---|---|
| 3,715,374 | 2/1973 | De Luca et al. | 514/168 |
| 4,021,423 | 5/1977 | Baggiolini | 549/453 |
| 4,028,349 | 6/1977 | Partridge, Jr. et al. | 540/116 |
| 4,224,231 | 9/1980 | De Luca et al. | 552/653 |
| 4,758,382 | 7/1988 | Sterling et al. | 552/653 |
| 4,997,824 | 3/1991 | Popovtzer et al. | 514/170 |
| 5,001,118 | 3/1991 | Maeda et al. | 514/167 |

FOREIGN PATENT DOCUMENTS 0198213  10/1986  European Pat. Off. .

OTHER PUBLICATIONS

Bone, vol. 6, No. 2, 1985, pp. 113–123, I. Atkin et al, "Effects of Vitamin D metabolites on healing of low phosphate, Vitamin D deficient induced rickets in rats".

Bell Biology International Reports, vol. 12, No. 5, May 1988, pp. 373–381, E. Blaugrund et al., "Responses of rachitic cartilage cells to metabolites of Vitamin D3".

Archives Of Biochemistry And Biophysics, vol. 170, No. 2, 1975, pp. 620–626, Y. Tanaka et al, "Determination of stereochemical configuration of the 24-hydroxyl group of 24,25-dihydroxyvitamin D3 . . . ".

*Primary Examiner*—Theodore J. Criares
*Attorney, Agent, or Firm*—Sughrue, Mion, Zinn, Macpeak & Seas

[57] ABSTRACT

A pharmaceutical composition containing 24,25-dihydroxycholecalciferol is provided. The active ingredient used in the present invention is an intrinsic and safe substance, and so does not exhibit hypercalcemia which is the side effect induced by conventional antirachitic agents, and is effective for the treatment of rickets, particularly vitamin D resistant rickets.

1 Claim, No Drawings

24R,25-DIHYDROXYCHOLECALCIFEROL TO TREAT VITAMIN D RESISTANT RICKETS

This is a continuation of application Ser. No. 08/079,551, filed on Jun. 22, 1993.

BACKGROUND OF THE INVENTION

1. Field of the Invention

The present invention relates to a pharmaceutical composition, particularly an antirachitic agent, containing as an active ingredient 24,25-dihydroxycholecalciferol [that is, 24,25-dihydroxyvitamin $D_3$: hereinafter abbreviated to as "24,25-$(OH)_2$-$D_3$" or "the present active substance"]. More particularly, the present invention relates to a method for treating vitamin D resistant rickets.

2. Description of the Related Art

Rickets has recently become a relatively rare disease, but intractable rickets continues to occur at a high frequency. For example, vitamin D resistant rickets often offers difficulty in treatment. Almost all the vitamin D resistant rickets suffers from a congenital metabolic disorder inherited from the X-chromosomal dominant inheritance. The initial symptoms are bowlegs and a waddling gait. Further, it is believed that the vitamin D resistant rickets is characterized in that other abnormalities are not observed in general state and depression in myodynamia or the like is not observed either, unlike other types of rickets. Pathophysiology thereof still remains unknown in many points. Although administration of vitamin D in a large amount was performed in treating vitamin D resistant rickets, improvement thereof was considered difficult (for example, see *Dorland's Illustrated Medical Dictionary*, Hirokawa Shoten, 1980, p. 1611). Further, a large amount of 1α-hydroxycholecalciferol [hereinafter abbreviated to as "1α-(OH)-$D_3$"], 1α,25-dihydroxycholecalciferol [hereinafter abbreviated to as "1α,25-$(OH)_2$-$D_3$"], vitamin $D_2$, neutral phosphate, or the like was used.

However, it is widely known that 1α,25-$(OH)_2$-$D_3$, 1α-(OH)-$D_3$, vitamin $D_2$, neutral phosphate, or the like brings about many side effects. That is, hypercalcemia occurs frequently, and long term administration causes nephrocalcinosis. Further, it have been reported in many articles that hyperparathyroidism is induced, and renal calculus is formed by urine containing excessive oxalate mainly produced by the administration of neutral phosphate, and the like (for example, see *Internal Medicine*, Vol. 69, No. 4, pp. 687 to 690, 1992). Therefore, in view of the serious problem of side effects in treating vitamin D resistant rickets, there has been a desire for developing a more effective and safer therapeutic medicine which is free of such side effects.

SUMMARY OF THE INVENTION

The present inventors engaged in studies to eliminate the side effects accompanying conventional therapeutic agents and develop a safe therapeutic agent, and thereupon found that 24,25-$(OH)_2$-$D_3$, which exists in the healthy human body and has been proven to be safe, remedies vitamin D resistant rickets without inducing hypercalcemia which is the side effect exhibited by the conventional 1α,25-$(OH)_2$-$D_3$, 1α-(OH)-$D_3$, etc. The present invention is based on the above findings.

Therefore, the present invention relates to a pharmaceutical composition containing as an active ingredient 24,25-dihydroxycholecalciferol, that is, 24,25-$(OH)_2$-$D_3$.

DESCRIPTION OF THE PREFERRED EMBODIMENTS

The active ingredient of the present invention, that is, 24,25-$(OH)_2$-$D_3$, is a known compound described, for example, in *Pharmacia*, 10, pp. 319 to 322 (1974). As mentioned above, its existence in the healthy human body is known, but its physiological activity remains still unknown. There was a report relating to the physiological activity of 24,25-$(OH)_2$-$D_3$ on cartilage, but its antirachitic activity has not been known hitherto.

The 24,25-$(OH)_2$-$D_3$ used in the present invention involves the isomers of 24R,25-$(OH)_2$-$D_3$ and 24S,25-$(OH)_2$-$D_3$. In the present invention, 24R,25-$(OH)_2$-$D_3$, 24S,25-$(OH)_2$-$D_3$, or the racemes may be used, but 24R,25-$(OH)_2$-$D_3$ is particularly preferable.

The present active substance may preferably be effectively used for the treatment of vitamin D resistant rickets, but is also effective against general forms of rickets, for example, rickets of malabsorption syndrome, gluten sensitive enteropathy, hepatic failure, pseudo vitamin D dependency, vitamin D dependency, Lignac-Fanconi syndrome, idiopathic Fanconi's syndrome, Low's syndrome, phosphorus deficiency, Wilson's disease, tyrosinemia, fluorosis, hypophosphatasia, etc.

The acute toxicity of the present active substance was examined and the results are as follows:

The present active substance [24R,25-$(OH)_2$-$D_3$] was mixed with sesame oil containing 0.5% ethanol and orally administered to male and female ICR mice (body weight: 29 to 33 g for males and 22 to 29 g for females; 4 groups; each group consisting of five mice). No toxic symptoms were observed over the period of two weeks after administered. The $LD_{50}$ value was determined from the rate of death during said two weeks to find 215 mg/kg for males and 253 mg/kg for females.

The antirachitic activity of the present active substance can be determined, for example, using model mice for human hypophosphatemic vitamin D resistant rickets (vide infra Example 1). That is, when the present active substance is administered in an amount of 1 to 1000 μg/kg, the body weight, thighbone length, and serum phosphorus value are increased, in comparison with unadministered groups, but the serum calcium value does not change. Therefore, the present active substance administered will not cause hypercalcemia. Further, the ratio of unmineralized bone, a typical tissue of rickets, is also reduced.

The pharmaceutical composition of the present invention (particularly, the antirachitic agent) comprises the present active substance [24,25-$(OH)_2$-$D_3$] and a pharmaceutically acceptable additive or carrier. By selecting the additives, the composition may be formulated for the various administration routes as those of ordinary medicines, for example, intraperitoneal, oral or intramucosal administration or administration by injections.

The oral formulations are, for example, dispersions, powders, granules, pills, tablets, soft capsules, hard capsules, liquids, suspensions, emulsions, spirits, syrups, and dry syrups.

The injections are, for example, aqueous suspension injections, emulsions, intravenous injections, and so on.

The intramucosal formulations is, for example, suppositories.

As the pharmaceutical additives for the use of solid preparations like dispersions, powders, granules, tablets, and hard capsules, there may be mentioned cellulose derivatives, such as crystalline cellulose, methyl cellulose, hydroxypropylcellulose, low substituted hydroxypropylcellulose, hydroxypropyl-methylcellulose, hydroxypropylcellulose phthalate, hydroxypropyl-methylcellulose acetate succinate, carmellose, carmellose calcium, carmellose sodium, cross-carmellose sodium, carboxymethylethyl-cellulose, or hydroxyethylcellulose; starches or the derivatives thereof, such as wheat, rice, corn or potato starch, dextrin, pregelatinized starch, hydroxypropyl starch, or carboxymethylstarch sodium; synthetic polymers, such as polyvinylpyrrolidone, aminoacrylmethacrylate copolymers, methacrylate copolymers, polyvinylacetal diethylaminoacetate, or polyvinyl alcohol; natural polymers, such as acacia or shellac; sugars, such as lactose, purified sucrose, mannitol, or glucose; fatty acids or the metallic salts thereof, such as stearic acid, or aluminum, calcium or magnesium stearate; macrogols such as macrogol 6000; inorganic compounds, such as hydrate silicon dioxide, light anhydrous silicic acid, synthetic aluminum silicate, synthetic hydrotalcite, dried aluminum hydroxide gel, talc, precipitated calcium carbonate, magnesium aluminometasilicate, dibasic calcium phosphate. The above compound may be used alone or in the form of a mixture of two or more said compounds as excipients, disintegrators, binders, lubricants, coating agents, etc. The administration of calcium is effective in remedying ticket patients, and so a pharmaceutical composition of the present invention containing precipitated calcium carbonate as an excipient is particularly preferable. Further, a combination of the present active substance and a derivative of a calcium compound is particularly effective in treating rickets. As examples of the combination, there may be mentioned mixtures with calcium lactate, calcium chloride, calcium monohydrogenphosphate, calcium dihydrogenphosphate, calcium gluconate, and calcium L-aspartate.

The solvents for the internal solution in the soft capsules may be for example oily substances, such as medium-chain fatty acid triglycerides, macrogols such as macrogol 300 or macrogol 400, glycerol, sesame oil, cotton seed oil, olive oil, rape seed oil, camellia oil, corn oil, soybean oil, safflower oil, orange oil, eucalyptus oil, peanut oil, or wheat germ oil. The coating component of the soft capsule shell comprises a combination of gelatin, glycerol, sorbitol, macrogol, titanium oxide, calcium carbonate, sugars, preservatives, coloring agents, etc. As the preservatives, p-hydroxybenzoate esters are often used.

The oral solution formulations such as liquids, emulsions, suspensions, spirits, or syrups may be prepared by dissolving or suspending the present active substance in water, ethanol, or the various oily substances which may be used as said internal solutions of the soft capsules, alone or in the form of a mixture. In this case, suitable additives may further be added.

The emulsions may be prepared by adding the present active substance into a suitable oil component, particularly a medium-chain fatty acid triglyceride and/or vegetable oil, and mixing with a suitable emulsifier and water to be emulsified. As a preferable emulsifier, there may be mentioned hydroxypropylcellulose, carboxyvinyl polymers, acacia, calcium stearate, propylene glycol, macrogols, sucrose esters of fatty acids, polyoxyl 40 stearate, polyoxyethylene hydrogenated castor oil, polyoxyethylene polyoxypropylene glycols, polysorbate 40, polysorbate 60, polysorbate 80, sodium lauryl sulfate, lauromacrogol, etc. In this case, a suitable emulsion stabilizer may also be added.

The suspensions may be prepared by pulverizing the present active substance by a suitable method and suspending in an aqueous solvent. A suitable suspending agent or suspension stabilizer may be added thereto. As the suspending agents, there may be preferably mentioned crystalline cellulose, methyl cellulose, hydroxypropyl cellulose, hydroxypropylmethyl cellulose, polyvinylpyrrolidone, carboxyvinyl polymers, gelatin, tragacanth, aluminum stearate, sucrose esters of fatty acids, polyoxyethylene hydrogenated castor oils, sorbitan fatty acid esters, etc. As the emulsion stabilizer, there may be mentioned sugars, higher fatty alcohols, polyvinyl alcohol, polyvinylpyrrolidone, and macrogols. Further, by adding suitable calcium salts to the above oral liquid formulations, a synergistic effects in treating rickets may be expected as in the above oral solid formulations.

Suitable coloring agents, perfumes, solubilizing agents, antioxidants, preservatives, or the like may also be added to the above oral formulations. The antioxidants are, for example, butylhydroxyanisole, propyl gallate, dibutylhydroxy-toluene, and $\alpha$-tocopherol. The preservatives are, for example, sorbic acid or the salts thereof, paraoxybenzoates, chlorobutanol, benzalkonium chloride, and benzyl alcohols.

The injections may be prepared by dissolving or suspending the present active substance in water or a suitable oily solvent. When preparing an aqueous injections, a suitable solubilizing agent is added to the water. The solubilizing agents are preferably, for example, polyoxyethylene hydrogenated castor oils, polyoxyethylene sorbitan esters, sorbitan fatty acid esters, macrogols, polypropylene glycol, mannitol, ethanol, etc.

The aqueous suspension injections and emulsions may be prepared in the same manner as the above oral suspensions and emulsions. It is possible further to add agents acceptable to the injections, such as analgesics, antioxidants, preservatives, pH adjustors, isotonizing agents and so on.

Suppositories may be prepared by melting the present active substance in a base such as hard fats, cacao butter, macrogols, or the like. A suitable dispersing agent, stabilizer, antioxidant or the like may also be added to the suppositories.

The present active substance may be contained in an administration unit in an amount effective for exhibiting the antirachitic activity, preferably 0.00002 to 4 percent by weight, more preferably 0.0002 to 1 percent by weight. Further, the present active substance may be administered in an amount of 0.1 to 100,000 μg, preferably 10 to 60,000 μg per day for an adult.

EXAMPLES

The present invention will now be further illustrated by, but is by no means limited to, the following examples.

Example 1

24R,25-$(OH)_2$-$D_3$, 24,25-$(OH)_2$-$D_3$ (racemate of 24R and 24S), and 1α,25-$(OH)_2$-$D_3$ were administered continuously for 28 days intraperitoneally to 4 weeks old Hyp mice (vitamin D resistant ticket model). As the solvent, 0.75% ethanol/Tween 80 was used. As the test Groups, the following 13 Groups I to XIII each comprising seven mice were used:

I: Solvent control group,

II: 24R,25-$(OH)_2$-$D_3$; 1 μg/kg,

III: 24R,25-$(OH)_2$-$D_3$; 10 μg/kg,

IV: 24R,25-$(OH)_2$-$D_3$; 100 μg/kg,

V: 24R,25- $(OH)_2$-$D_3$; 1000 μg/kg,

VI: 24,25-$(OH)_2$-$D_3$; 1 μg/kg,

VII: 24,25-$(OH)_2$-$D_3$; 10 μg/kg,

VIII: 24,25-$(OH)_2$-$D_3$; 100 μg/kg,

IX: 24,25-$(OH)_2$-$D_3$; 1000 μg/kg,

X: 1α,25-$(OH)_2$-$D_3$; 0.01 μg/kg,

XI: 1α,25-$(OH)_2$-$D_3$; 0.1 μg/kg,

XII: 1α,25-$(OH)_2$-$D_3$; 1 μg/kg,

XIII: 1α,25-$(OH)_2$-$D_3$; 10 μg/kg.

After administering, the body weights were measured and bloods were taken from the hearts. Further, the femora were excised and the lengths thereof were measured. Further, the fifth vertebrae were excised, dehydrated and fixed by 70% ethanol to prepare unmineralized specimens. The specimens were stained with the Villanueva Goldnet, and the ratio of unmineralized bone increased due to the rickets was measured using an image analyzer (Pias 550). The results are shown in Tables 1 to 3.

TABLE 1

|  | Body weight (g) | Femur length (mm) |
|---|---|---|
| *Control group* | | |
| I | 14.8 ± 2.6 | 10.2 ± 0.5 |
| *24R,25-(OH)$_2$—D$_3$ groups* | | |
| II | 16.0 ± 2.2 | 10.5 ± 0.5 |
| III | 16.9 ± 2.3 | 10.7 ± 0.5 |
| IV | 17.0 ± 1.3 | 10.6 ± 0.4 |
| V | 18.8 ± 2.7[1)] | 11.6 ± 0.7[2)] |
| *24,25-(OH)$_2$—D$_3$ (racemate) groups* | | |
| VI | 15.1 ± 3.0 | 10.5 ± 0.4 |
| VII | 15.8 ± 2.3 | 10.7 ± 0.6 |
| VIII | 16.3 ± 1.2 | 10.6 ± 0.8 |
| IX | 16.5 ± 2.2 | 10.5 ± 0.5 |
| *1α,25-(OH)$_2$—D$_3$ groups* | | |
| X | 16.0 ± 1.9 | 10.6 ± 0.6 |
| XI | 13.8 ± 3.7 | 11.2 ± 0.7[3)] |
| XII | 11.4 ± 1.6[1)] | 10.1 ± 0.5 |
| XIII | 8.5 ± 1.0[1)] | 9.8 ± 0.4 |

[1)]: $p < 0.05$, [2)]: $p < 0.001$, [3)] $p < 0.01$ (vs control group)

TABLE 2

Concentration of Serum Calcium and Inorganic Phosphorus of Each Group

|  | Serum Ca (mg/dl) | Serum Pi (mg/dl) |
|---|---|---|
| *Control group* | | |
| I | 10.2 ± 0.8 | 5.3 ± 0.8 |
| *24R,25-(OH)$_2$—D$_3$ groups* | | |
| II | 9.2 ± 0.9 | 6.9 ± 1.3[1)] |
| III | 10.0 ± 1.0 | 7.3 ± 0.8[2)] |
| IV | 9.5 ± 1.5 | 8.6 ± 1.1[2)] |
| V | 10.1 ± 1.2 | 9.2 ± 1.1[2)] |
| *24,25-(OH)$_2$—D$_3$ (racemate) groups* | | |
| VI | 9.5 ± 0.8 | 5.8 ± 1.0 |
| VII | 10.7 ± 0.9 | 5.4 ± 0.8 |
| VIII | 10.0 ± 1.1 | 6.4 ± 1.2 |
| IX | 10.5 ± 0.9 | 6.8 ± 0.7[2)] |
| *1α,25-(OH)$_2$—D$_3$ groups* | | |
| X | 10.6 ± 0.9 | 8.7 ± 1.9[2)] |
| XI | 11.8 ± 1.2[1)] | 10.5 ± 0.5[2)] |
| XII | 14.8 ± 1.3[2)] | 9.8 ± 1.1[2)] |
| XIII | 15.2 ± 0.9[2)] | 9.7 ± 1.1[2)] |

[1)]: $p < 0.05$, [2)]: $p < 0.001$ (vs control group)

TABLE 3

Ratio of Unmineralized Bone by Histological Measurement of Each Group

|  | Unmineralized bone volume/ Bone volume (%) |
|---|---|
| *Control group* | |
| I | 51.2 ± 5.9 |
| *24R,25-(OH)$_2$—D$_3$ groups* | |
| II | 45.3 ± 7.2 |
| III | 40.9 ± 5.6[1)] |
| IV | 34.3 ± 5.1[2)] |
| V | 22.0 ± 7.3[2)] |
| *24,25-(OH)$_2$—D$_3$ (racemate) groups* | |
| VI | 50.3 ± 4.9 |
| VII | 48.1 ± 6.6 |
| VIII | 42.3 ± 6.7[3)] |
| IX | 35.8 ± 5.2[2)] |
| *1α,25-(OH)$_2$—D$_3$ groups* | |
| X | 47.5 ± 3.8 |
| XI | 28.3 ± 6.2[2)] |
| XII | 20.5 ± 8.3[2)] |
| XIII | 18.8 ± 5.6[2)] |

[1)]: $p < 0.01$, [2)]: $p < 0.001$, [3)] $p < 0.05$ (vs control group)

The above results may be summarized as follows:

One of the present active substances, that is, 24R,25-(OH)$_2$-D$_3$ (groups II to V) increased the body weight of the mice in a dose dependent manner. Particularly, the group V showed a significant increase with the increase of the body weight, the femur length was also increased, and particularly, the group V also showed the significant increase in this regard as above. Further, an increase in the body weight was observed also for the racemate of the present active substance, that is, 24,25-(OH)$_2$-D$_3$ (groups VI to IX). The femur length was also increased, but less than the length increased by said 24R,25-(OH)$_2$-D$_3$. On the other hand, the comparative substance, i.e., 1α,25-(OH)$_2$-D$_3$ (groups X to XIII) reduced the body weight in a dose dependent manner, except that only the group X showed an increase in the body weight. Further, the femur length was increased significantly only in the group XI.

No significant change of the serum calcium concentration was observed in each group of the present active substances, i.e., 24R,25-(OH)$_2$-D$_3$ and 24,25-(OH)$_2$-D$_3$ (racemate), but the concentration was significantly increased in the comparative substance, i.e., 1α,25-(OH)$_2$-D$_3$ (groups XII and XIII). That means hypercalcemia. Further, the serum inorganic phosphorus concentration was significantly increased in the present active substance, 24R,25-(OH)$_2$-D$_3$ and the comparative substance, i.e., the 1α,25-(OH)$_2$-D$_3$. In the other present active substance, i.e., 24,25-(OH)$_2$-D$_3$ (racemate), a significant increase was observed in the maximum dosage, that is, the group IX.

Further, the ratio of the unmineralized bone (typical tissue structure in rickets), which was high in the control group, was examined by bone histomorphometrical measurement, whereupon a dosage dependent significant reduction was observed in both of the present active substance, 24R,25-(OH)$_2$-D$_3$ and the comparative substance, 1α,25-(OH)$_2$-D$_3$. Furthermore, a significant reduction was observed in the maximum dosage group of the present active substance (racemate), 24,25-(OH)$_2$-D$_3$.

Example 2

24R,25-(OH)$_2$-D$_3$ (200 mg) was dissolved in ethanol (5 ml), and sesame oil (2 kg) was added and dissolved. Then, highly pure argon gas was bubbled in the sesame oil solution to remove the residual oxygen. Thereafter, soft capsules were produced by an ordinary method, using a soft capsule preparing machine so that each capsule contained 10 µg of 24R,25-(OH)$_2$-D$_3$.

The coating component of the soft capsule shell had the following composition (parts by weight in the final form)

| | |
|---|---|
| Gelatin | 10 parts by weight |
| Glycerol | 2 parts by weight |
| Preservative (ethylparabene) | 0.05 part by weight |
| Titanium white | 0.2 part by weight |
| Water | 0.2 part by weight |

Although the present invention has been described with reference to specific embodiments, various changes and modifications obvious to those skilled in the art are deemed to be within the spirit, scope, and concept of the invention.

We claim:

1. A method for treating vitamin D resistant rickets of an animal, comprising administering to said animal a therapeutically effective amount of a composition comprising 24R, 25-dihydroxycholecalciferol and a pharmaceutically acceptable carrier.

* * * * *

UNITED STATES PATENT AND TRADEMARK OFFICE
CERTIFICATE OF CORRECTION

PATENT NO. : 5,508,274
DATED : April 16, 1996
INVENTOR(S) : Yoshiki SEINO et al.

It is certified that error appears in the above-indentified patent and that said Letters Patent is hereby corrected as shown below:

Change "—$D_3$" to ---$D_3$-- in Tables 1, 2 and 3
Change "$^{1)}$:p<" to --1):p<-- in Tables 1, 2 and 3
Change "$^{2)}$:p<" to --2):p<-- in Tables 1, 2 and 3
Change "$^{3)}$:p<" to --3):p<-- in Tables 1 and 3
Change "24$R_{,25}$." to --24$R,25$--- in column 6, line 50

Signed and Sealed this

Twenty-eighth Day of January, 1997

Attest:

BRUCE LEHMAN

Attesting Officer     Commissioner of Patents and Trademarks